US009180045B2

(12) United States Patent
Lazar

(10) Patent No.: US 9,180,045 B2
(45) Date of Patent: Nov. 10, 2015

(54) TREATMENT MEDIUM DELIVERY DEVICE AND METHODS FOR DELIVERY OF SUCH TREATMENT MEDIUMS TO THE EYE USING SUCH A DELIVERY DEVICE

(75) Inventor: Eliot Lazar, Orchard Park, NY (US)

(73) Assignee: Mati Therapeutics Inc., Austin, TX (US)

( * ) Notice: Subject to any disclaimer, the term of this patent is extended or adjusted under 35 U.S.C. 154(b) by 1220 days.

(21) Appl. No.: 13/081,865

(22) Filed: Apr. 7, 2011

(65) Prior Publication Data
US 2011/0202020 A1 Aug. 18, 2011

Related U.S. Application Data

(63) Continuation of application No. 11/571,147, filed as application No. PCT/US2005/023848 on Jul. 1, 2005, now Pat. No. 7,922,702.

(60) Provisional application No. 60/585,287, filed on Jul. 2, 2004.

(51) Int. Cl.
*A61F 9/00* (2006.01)
*A61F 9/007* (2006.01)

(52) U.S. Cl.
CPC ........... *A61F 9/0017* (2013.01); *A61F 9/00772* (2013.01)

(58) Field of Classification Search
CPC . A61F 9/0017; A61F 9/00772; A61K 9/0048; A61K 9/0051; A61L 31/16; A61L 27/54; A61L 31/10
USPC ................ 604/500, 289, 294, 297, 298, 300, 604/890.1, 891.1, 892.1, 93.01; 424/427, 424/423
See application file for complete search history.

(56) References Cited

U.S. PATENT DOCUMENTS

| 3,865,108 A | | 2/1975 | Hartop | |
|---|---|---|---|---|
| 3,867,519 A | * | 2/1975 | Michaels | 424/473 |
| 3,949,750 A | * | 4/1976 | Freeman | 424/427 |
| 4,014,335 A | | 3/1977 | Arnold | |
| 4,186,184 A | * | 1/1980 | Zaffaroni | 424/427 |
| 4,281,654 A | | 8/1981 | Shell et al. | |
| 4,660,546 A | | 4/1987 | Herrick et al. | |
| 4,828,840 A | * | 5/1989 | Sakamoto et al. | 424/474 |

(Continued)

FOREIGN PATENT DOCUMENTS

| EP | 0442745 A1 | 8/1991 |
|---|---|---|
| EP | 0621022 A1 | 10/1994 |

(Continued)

OTHER PUBLICATIONS

European Search Report and Search Opinion as issued for European Patent Application No. 11173692.2, dated Sep. 14, 2011.

(Continued)

*Primary Examiner* — Manuel Mendez
(74) *Attorney, Agent, or Firm* — Koren Anderson; Mati Therapeutics Inc.

(57) ABSTRACT

A device for delivering a treatment medium to an eye includes a first body portion configured to be removably inserted and secured in an opening of the eye, and a second body portion supported by the first body portion. At least the second body portion includes a treatment medium, and a coating having an opening through which the treatment medium elutes out of the device.

12 Claims, 3 Drawing Sheets

(56) References Cited

U.S. PATENT DOCUMENTS

| | | |
|---|---|---|
| 4,886,488 A | 12/1989 | White |
| 4,915,684 A | 4/1990 | MacKeen et al. |
| 4,959,048 A | 9/1990 | Seder et al. |
| 5,041,081 A | 8/1991 | Odrich |
| 5,049,142 A | 9/1991 | Herrick et al. |
| 5,053,030 A | 10/1991 | Herrick et al. |
| 5,098,443 A | 3/1992 | Parel et al. |
| 5,128,058 A | 7/1992 | Ishii et al. |
| 5,133,159 A | 7/1992 | Nelson |
| 5,163,959 A | 11/1992 | Herrick |
| 5,171,270 A | 12/1992 | Herrick |
| 5,283,063 A * | 2/1994 | Freeman ............... 424/427 |
| 5,318,513 A | 6/1994 | Leib |
| 5,334,137 A * | 8/1994 | Freeman ................ 604/8 |
| 5,378,475 A * | 1/1995 | Smith et al. ............ 424/473 |
| 5,395,618 A | 3/1995 | Darougar et al. |
| 5,417,651 A | 5/1995 | Guena et al. |
| 5,423,777 A | 6/1995 | Tajiri et al. |
| 5,466,233 A | 11/1995 | Weiner et al. |
| 5,556,633 A | 9/1996 | Haddad et al. |
| 5,707,643 A | 1/1998 | Ogura et al. |
| 5,723,005 A | 3/1998 | Herrick |
| 5,728,751 A * | 3/1998 | Patnaik ............... 523/112 |
| 5,741,881 A * | 4/1998 | Patnaik ............... 528/75 |
| 5,766,243 A | 6/1998 | Christensen et al. |
| 5,770,589 A | 6/1998 | Billson et al. |
| 5,773,019 A * | 6/1998 | Ashton et al. ........ 424/423 |
| 5,795,591 A | 8/1998 | Lee et al. |
| 5,824,073 A | 10/1998 | Peyman |
| 5,826,584 A | 10/1998 | Schmitt |
| 5,830,171 A | 11/1998 | Wallace |
| 5,840,054 A | 11/1998 | Hamano et al. |
| 5,961,370 A | 10/1999 | Valle et al. |
| 5,962,383 A | 10/1999 | Doyel et al. |
| 5,993,407 A | 11/1999 | Moazed |
| 6,010,391 A | 1/2000 | Lewellen et al. |
| 6,016,806 A | 1/2000 | Webb |
| 6,027,470 A | 2/2000 | Mendius |
| 6,041,785 A | 3/2000 | Webb |
| 6,082,362 A | 7/2000 | Webb |
| 6,095,901 A | 8/2000 | Robinson et al. |
| 6,149,684 A | 11/2000 | Herrick |
| 6,196,993 B1 | 3/2001 | Cohan et al. |
| 6,234,175 B1 | 5/2001 | Zhou et al. |
| 6,238,363 B1 | 5/2001 | Kurihashi |
| 6,254,562 B1 | 7/2001 | Fouere |
| 6,264,971 B1 | 7/2001 | Darougar et al. |
| 6,290,684 B1 | 9/2001 | Herrick |
| 6,306,114 B1 | 10/2001 | Freeman et al. |
| 6,331,313 B1 | 12/2001 | Wong et al. |
| 6,371,122 B1 | 4/2002 | Mandelkorn |
| 6,375,972 B1 * | 4/2002 | Guo et al. ............ 424/423 |
| 6,383,192 B1 | 5/2002 | Kurihashi |
| 6,428,502 B1 | 8/2002 | Lang |
| 6,455,062 B1 | 9/2002 | Olejnik et al. |
| 6,605,108 B2 | 8/2003 | Mendius et al. |
| 6,629,533 B1 | 10/2003 | Webb et al. |
| 6,699,282 B1 | 3/2004 | Sceusa |
| 6,706,034 B1 | 3/2004 | Bhat |
| 6,706,275 B1 | 3/2004 | Camp |
| 6,729,939 B2 | 5/2004 | Wrue |
| 6,756,049 B2 | 6/2004 | Brubaker et al. |
| 6,780,164 B2 | 8/2004 | Bergheim et al. |
| 6,840,931 B2 | 1/2005 | Peterson et al. |
| 6,846,318 B2 | 1/2005 | Camp |
| 6,866,563 B2 | 3/2005 | Green |
| 6,964,781 B2 | 11/2005 | Brubaker |
| 6,982,090 B2 | 1/2006 | Gillespie |
| 6,991,808 B2 | 1/2006 | Brubaker et al. |
| 6,994,684 B2 | 2/2006 | Murray et al. |
| 7,017,580 B2 | 3/2006 | Prescott et al. |
| 7,117,870 B2 | 10/2006 | Prescott |
| 7,135,009 B2 | 11/2006 | Tu et al. |
| 7,204,253 B2 | 4/2007 | Mendius et al. |
| 7,204,995 B2 | 4/2007 | El-Sherif et al. |
| 7,708,711 B2 * | 5/2010 | Tu et al. ............... 604/8 |
| 2002/0032400 A1 | 3/2002 | Moazed |
| 2002/0110635 A1 | 8/2002 | Brubaker et al. |
| 2002/0151960 A1 | 10/2002 | Mendius et al. |
| 2002/0198453 A1 | 12/2002 | Herrick, II |
| 2003/0064088 A1 * | 4/2003 | Carvalho et al. ........ 424/423 |
| 2003/0130612 A1 | 7/2003 | Moazed |
| 2004/0102729 A1 | 5/2004 | Haffner et al. |
| 2004/0121014 A1 | 6/2004 | Guo et al. |
| 2004/0127843 A1 | 7/2004 | Tu et al. |
| 2004/0141151 A1 | 7/2004 | Gillespie |
| 2004/0147870 A1 | 7/2004 | Burns |
| 2004/0170685 A1 | 9/2004 | Carpenter et al. |
| 2004/0175410 A1 | 9/2004 | Ashton et al. |
| 2004/0249333 A1 | 12/2004 | Bergheim et al. |
| 2004/0265356 A1 | 12/2004 | Mosack |
| 2005/0048121 A1 | 3/2005 | East et al. |
| 2005/0095269 A1 | 5/2005 | Ainpour et al. |
| 2005/0129731 A1 | 6/2005 | Horres et al. |
| 2005/0197614 A1 | 9/2005 | Pritchard et al. |
| 2005/0220882 A1 | 10/2005 | Pritchard et al. |
| 2005/0232972 A1 | 10/2005 | Odrich et al. |
| 2005/0244469 A1 | 11/2005 | Whitcup et al. |
| 2005/0266047 A1 | 12/2005 | Tu et al. |
| 2005/0271704 A1 | 12/2005 | Tu et al. |
| 2005/0283109 A1 | 12/2005 | Peyman |
| 2006/0013835 A1 | 1/2006 | Anderson et al. |
| 2006/0020248 A1 | 1/2006 | Prescott |
| 2006/0020253 A1 | 1/2006 | Prescott |
| 2006/0074370 A1 | 4/2006 | Zhou |
| 2006/0106352 A1 | 5/2006 | Kurihashi |
| 2006/0122553 A1 | 6/2006 | Hanna |
| 2007/0083146 A1 | 4/2007 | Murray |
| 2007/0123924 A1 | 5/2007 | Becker |
| 2007/0132125 A1 | 6/2007 | Rastogi et al. |
| 2007/0135914 A1 | 6/2007 | Herrick, II |
| 2007/0243230 A1 | 10/2007 | de Juan et al. |
| 2007/0269487 A1 | 11/2007 | de Juan et al. |
| 2007/0298075 A1 | 12/2007 | Borgia et al. |
| 2007/0299515 A1 | 12/2007 | Herrick, II |
| 2007/0299516 A1 | 12/2007 | Cui |
| 2008/0038317 A1 | 2/2008 | Chang et al. |
| 2008/0045878 A1 | 2/2008 | Bergheim et al. |
| 2008/0045911 A1 | 2/2008 | Borgia et al. |
| 2009/0092654 A1 | 4/2009 | de Juan, Jr. et al. |
| 2009/0104248 A1 | 4/2009 | Rapacki et al. |
| 2009/0105749 A1 | 4/2009 | de Juan, Jr. et al. |
| 2009/1010424 | 4/2009 | Utkhede et al. |

FOREIGN PATENT DOCUMENTS

| | | |
|---|---|---|
| JP | 10-033584 | 2/1998 |
| JP | 2001-520550 | 10/2001 |
| JP | 2004-202276 | 7/2004 |
| JP | 2005-000628 | 1/2005 |
| JP | 2005-058622 | 3/2005 |
| JP | 2005-110930 | 4/2005 |
| JP | 2005110765 | 4/2005 |
| JP | 2005-312835 | 11/2005 |
| JP | 2005319190 | 11/2005 |
| JP | 2005-328922 | 12/2005 |
| JP | 2007-195819 | 8/2007 |
| WO | WO-98/33461 A1 | 8/1998 |
| WO | WO-98/42282 A1 | 10/1998 |
| WO | WO-99/37260 A1 | 7/1999 |
| WO | WO-99/44553 A1 | 9/1999 |
| WO | WO-99/64089 A1 | 12/1999 |
| WO | WO-99/65544 A1 | 12/1999 |
| WO | WO-00/27321 A1 | 5/2000 |
| WO | WO-00/62760 A1 | 10/2000 |
| WO | WO-02/11783 A1 | 2/2002 |
| WO | WO-02/058667 A2 | 8/2002 |
| WO | WO-02/083198 A2 | 10/2002 |
| WO | WO-03/017897 A2 | 3/2003 |
| WO | WO 03/020172 | 3/2003 |
| WO | WO-03/022242 A1 | 3/2003 |
| WO | WO-03/057101 A1 | 7/2003 |
| WO | WO-2004/004614 A2 | 1/2004 |
| WO | WO-2004/024043 A2 | 3/2004 |

(56) References Cited

FOREIGN PATENT DOCUMENTS

| WO | WO 2004/066979 | 8/2004 |
|---|---|---|
| WO | WO-2004/105658 A1 | 12/2004 |
| WO | WO-2004/112639 A2 | 12/2004 |
| WO | WO-2005/000154 A2 | 1/2005 |
| WO | WO-2005/086694 A2 | 9/2005 |
| WO | WO-2006/014434 A2 | 2/2006 |
| WO | WO-2006/031658 A2 | 3/2006 |
| WO | WO-2006/044669 A2 | 4/2006 |
| WO | WO-2006/057859 A1 | 6/2006 |
| WO | WO-2006/096586 A1 | 9/2006 |
| WO | WO-2007/008262 A2 | 1/2007 |
| WO | WO-2007/115259 A2 | 10/2007 |
| WO | WO-2007/115261 A2 | 10/2007 |
| WO | WO-2007/149771 A2 | 12/2007 |
| WO | WO-2007/149832 A2 | 12/2007 |
| WO | WO-2008/056060 A2 | 5/2008 |
| WO | WO-2008/094989 A2 | 8/2008 |
| WO | WO-2009/035562 A2 | 3/2009 |

OTHER PUBLICATIONS

Notice of Reasons for Rejection as issued for Japanese Patent Application No. 2007-520444, dated Feb. 15, 2012.
Examination Report as issued for European Patent Application No. 05768122.3, dated May 3, 2012.
Official Action as issued for Canadian Patent Application No. 2,572,592, dated Jun. 15, 2012.
"International Application Serial No. PCT/US2008/010479, International Search Report mailed Dec. 15, 2008", 6 pgs.
"International Application Serial No. PCT/US2008/010479, Written Opinion mailed Dec. 15, 2008", 7 pgs.
"U.S. Appl. No. 11/695,537, Notice mailed Nov. 28, 2008 Regarding a Non-compliant or Nonresponsive Amendment filed on Nov. 3, 2008", 3 pgs.
"U.S. Appl. No. 11/695,537, Restriction Requirement mailed Oct. 3, 2008", 10 pgs.
"U.S. Appl. No. 11/695,537, Response filed Nov. 3, 2008 to Restriction Requirement mailed Oct. 3, 2008", 15 pgs.
"U.S. Appl. No. 11/695,537, Response filed Dec. 17, 2008 to Office Communication mailed Nov. 28, 2008", 8 pgs.
"U.S. Appl. No. 11/695,545, Preliminary Amendment and Response filed Nov. 6, 2008 to Restriction Requirement mailed Oct. 6, 2008", 14 pgs.
"U.S. Appl. No. 11/695,545, Restriction Requirement mailed Oct. 6, 2008", 10 pgs.
"Chinese Application Serial No. 200580028979.2, First Office Action mailed Dec. 12, 2008", (English Translation), 7 pgs.
"Chinese Application Serial No. 200580028979.2, Second Office Action mailed Aug. 7, 2009", (English Translation), 3 pgs.
"Chinese Application Serial No. 200580028979.2, Response filed Jun. 24, 2009 to First Office Action mailed Dec. 12, 2008", (w/ English Translation of Claims), 15 pgs.
"European Application Serial No. 05768122.3, Supplementary European Search Report mailed on Mar. 31, 2009", 3 pgs.
"European Application Serial No. 05768122.3, Communication mailed Apr. 17, 2009", 6 pgs.
"European Application Serial No. 05768122.3, Office Action mailed Jul. 13, 2009", 3 pgs.
"International Application Serial No. PCT/US07/65792, International Search Report mailed on Nov. 20, 2008", 2 pgs.
"International Application Serial No. PCT/US07/65792, International Written Opinion mailed on Nov. 20, 2008", 5 pgs.
"International Application Serial No. PCT/US2007/065789, International Search Report mailed on Aug. 13, 2008", 3 pgs.
"International Application Serial No. PCT/US2007/065789, Written Opinion mailed on Aug. 13, 2008", 5 pgs.
"International Application Serial No. PCT/US2008/010487, International Search Report mailed May 25, 2009", 5 pgs.
"International Application Serial No. PCT/US2008/010487, Written Opinion mailed on May 25, 2009", 8 pgs.
De Juan, Jr., E., et al., "Expandable Nasolacrimal Drainage System Implants", U.S. Appl. No. 60/970,696, filed Sep. 7, 2007, 82 pgs.
De Juan, Jr., E., et al., "Manufacture of Expandable Nasolacrimal Drainage System Implants,"U.S. Appl. No. 60/970,720, filed Sep. 7, 2007, 57 pgs.
De Juan, Jr., E., et al., "Multiple Drug Delivery Systems and Combinations of Drugs With Punctal Implants", U.S. Appl. No. 60/970,820, Sep. 7, 2007, 67 pgs.
Reich, C., et al., "Nasolacrimal Drainage System Implants for Drug Delivery", U.S. Appl. No. 60/970,709, filed Sep. 7, 2007, 103 pgs.
Reich, Jr., Carl J., et al., "Manufacture of Drug Cores for Sustained Release of Therapeutic Agents", U.S. Appl. No. 60/970,699, filed Sep. 7, 2007, 66 pgs.
"Chinese Application No. 200580028979.2, Response filed Jun. 24, 2009 to First Office Action mailed Dec. 12, 2008", (w/ English Translation of claims), 15 pgs.
"Chinese Application No. 200580028979.2, Second Office Action mailed Aug. 7, 2009", (w/ English Translation), 9 pgs.
Notice of Reasons for Rejection as issued for Japanese Patent Application No. 2007-520444, dated Aug. 25, 2010.
International Search Report and Written Opinion as issued for PCT/US05/23848, dated May 15, 2006, 7 pgs.

\* cited by examiner

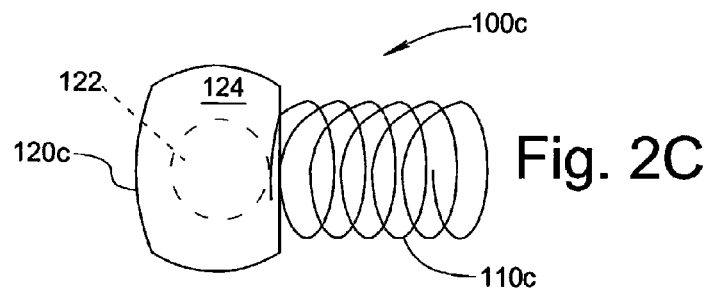
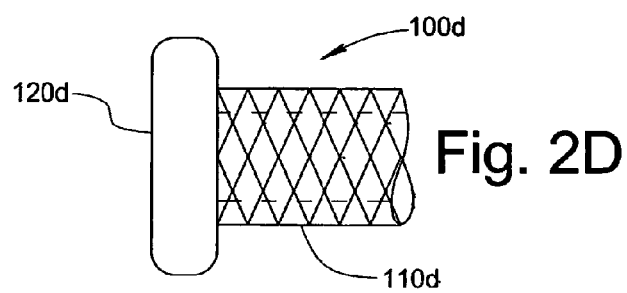
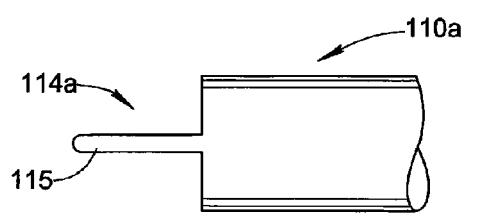
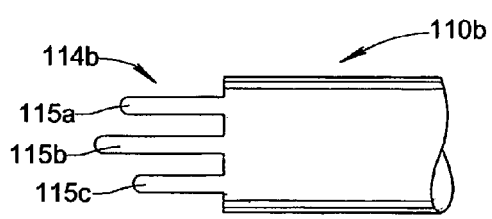
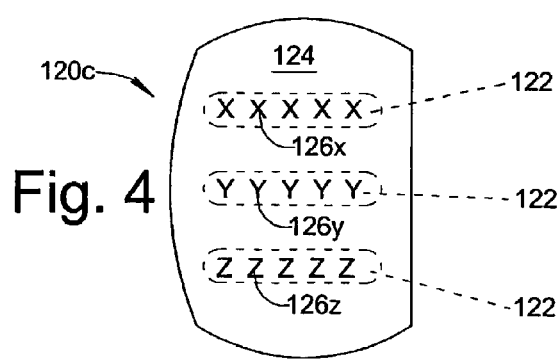

TREATMENT MEDIUM DELIVERY DEVICE AND METHODS FOR DELIVERY OF SUCH TREATMENT MEDIUMS TO THE EYE USING SUCH A DELIVERY DEVICE

CROSS-REFERENCE TO RELATED APPLICATIONS

This application is a continuation application of U.S. patent application Ser. No. 11/571,147, filed Dec. 21, 2006, which was the United States National Phase entry of International Patent Application No. PCT/US05/23848, filed Jul. 1, 2005, which claims the benefit of priority from U.S. Provisional Patent Application Ser. No. 60/585,287, filed Jul. 2, 2004. The contents of all three priority applications are incorporated herein by reference in their entireties.

FIELD OF INVENTION

The present invention relates to methods, devices and techniques for treating eyes, such as eyes of mammals having eye disorders or diseases, more particularly to methods, devices and techniques for delivery of or administering a therapeutic medium/agent or other treatment medium to the eye and more particularly a medium delivery device being disposed in a punctum of an eye and methods related thereto. Also featured are methods related thereto for treating eyes using such treatment medium delivery devices and prophylactic administration of such therapeutics or other treatment mediums to eyes.

BACKGROUND OF THE INVENTION

There are a number of surgical procedures for the eye in which a therapeutic medium is instilled postoperatively in or on the eye as well as a number of therapeutic or treatment procedures in which a therapeutic medium or another medium or fluid is instilled on the eye topically. For example, for Lasik, cataract and other refractive procedures anti-inflammatories such as-steroids and anti-infective drugs are topically administered post-operatively. Also, the treatment of corneal diseases such as corneal melts or post-operative management of corneal transplants also can involve the topical delivery of drugs to the eye. Further, drugs or therapeutic mediums are delivered topically for the treatment of inflammatory eye disorders or eye infectious disorders.

In addition to the administering of drugs postoperatively and/or prophylactic administration for treatment of eye disorders or diseases, there also can arise a need to maintain a desired level of moisture postoperatively as well for treating what is commonly referred to as dry eye over a short period or long period of time. With reference to FIG. 1, the lacrimal glands continuously secrete tears that bathe the cornea and conjunctiva of the eye that moisten these tissues as well providing a vehicle for removing or washing away foreign substances (e.g., particles) that alight on the external surface (e.g., conjunctiva) of the eye. As the tears being secreted drain from the eye through the nasolacrimal duct, the drainage of the tears may make it difficult to achieve the desired level of moisture. It also is possible that the amount of fluid that can be secreted is insufficient for achieving the desired level of moisture such as that which occurs with the dry eye condition.

There exist a wide range of procedures or techniques for accomplishing such treatment. In one technique, plugs, sometimes referred to as punctum plugs are inserted using appropriate medical techniques/procedures into at least one of the two punctums of the affected or given eye. The inserted plug occludes the at least one punctum thereby preventing the flow of any tears or fluid through the occluded punctum, to the tear drainage ducts (upper lacrimal canaliculus and lower lacrimal canaliculus) and thus through the nasolacrimal duct. With such plugging of a punctum, the tears or fluid being secreted do not easily drain from the eye and thus are retained in the eye. This is so because the secreted tears only can escape the eye either by flowing through the punctum that is not plugged or by the tears or fluid overflowing and exiting the eye such as that seen when one cries. In other techniques, the individual directly administers or topically administers artificial tears, restasis, allergen or other agents to the treatment the drying eye condition.

Treatment of ophthalmic conditions using drugs applied directly to the eye in either liquid or ointment form, (i.e., topical administration) is generally effective for treating problems involving the superficial surface of the eye and diseases that involve the cornea and anterior segment of the eye, such as for example, conjunctivitis. As indicated above, however, such topical eye drops, however, can drain from the eye through the nasolacrimal duct and into the systemic circulation. As a consequence, the medication available for treatment is thus diluted or reduced and the drainage also increases the risk of unwanted systemic side effects. Further, data also indicates that it is not unusual for up to 85% of topically applied agents to be removed by the eye's blink mechanism/reflex. In addition the conventional technique of delivering drugs in the form of topical eye drops is of little utility because the drug can be highly unstable and therefore not easily formulated for topical delivery.

The use of a topical insert for direct delivery of drugs to the eye has been contemplated/attempted, however, this method has been found not to be desirable as such conventional topical inserts typically require patient self-administration and thus education on their insertion into and removal from the eye. Consequently, this particular technique demands a certain degree of manual dexterity that can be problematic for geriatric patients who are particularly susceptible to certain eye disorders that appear age related. Also, in many instances such topical inserts may cause eye irritation and such conventional inserts are prone to inadvertent loss due to eyelid laxity. Further, as with topical administration techniques described above, the drug being delivered by such a topical inset is drained from the eye through the nasolacrimal duct and into the systemic circulation, thereby diluting or reducing the amount of the drug that is available for treatment and the drainage also increases the risk of unwanted systemic side effects. Thus, such conventional direct delivery devices have limited, if any at all, utility for providing an effective source of drugs.

It thus would be desirable to provide a new device that provides a more effective pathway for controlled, direct delivery or administration of drugs, therapeutic mediums or other treatment mediums to the eye as well as providing new methods, for delivery of such drugs, therapeutic mediums or other treatment mediums (e.g., artificial tears) to the eye using such devices. It would be particularly desirable to provide such a device and method that would be more effective in delivering the medium topically as well as being retained within the eye in comparison to the prior art technique of direct delivery of the treatment medium/drug. It also would be desirable to provide such a device that can be adapted to delivery any of a number of drugs, therapeutic mediums, or other treatment mediums without changing the basic delivery concept. It also would be desirable to provide such a device that is adapted for removable insertion into an exiting bodily orifice of the eye, the punctum, whereby the device is retained there during normal eye activity as compared to prior art devices. It also would be desirable to provide a device that is adapted to provide a controllably releasable source of drugs, therapeutic medium or other treatment medium for administration over a desired period of time as compared to existing topical administration techniques.

SUMMARY OF THE INVENTION

The present invention features a device for delivering a treatment medium to an eye as well as methods related thereto. Such devices and methods allow a desired amount of the treatment medium to be delivered in a controllable manner over a predetermined time period directly to the eye. Such devices preferably are such as to allow medical personnel to localize the device to a delivery site within the eye (e.g., within a natural opening or orifice of the eye) for delivery of the treatment medium and removal by such medical personnel following such a treatment process.

In more particular embodiments, the delivery device is configured and arranged so that the treatment medium is eluted from one portion of the delivery device, thereby controllably delivering a desired amount of the treatment medium to the eye. In addition, the delivery device also is configured and arranged so that another portion thereof is removably secured within a natural opening or orifice in or proximal to the eye. In specific embodiments the another portion is configured and arranged so as to be removably secured within the natural opening comprising at least one punctum of an eye.

In further embodiments, the delivery device is configured and arranged such that when a delivery device is removably inserted into the one or both punctums, the delivery device occludes or plugs each punctum. Consequently, tears being secreted and/or the treatment medium being eluted from the delivery device is prevented from draining through the plugged punctum(s) and thus to the tear drainage ducts. This thereby necessarily increases the retention time of the treatment medium proximal the exterior surface of the eye as compared to conventional techniques. This increased retention time also necessarily provides a mechanism by which the treatment medium can traverse the barrier formed by such external surfaces such that the treatment medium can be delivered to other portions of the eye, for example, the anterior segment or portion of the eye.

In further embodiments the another portion of the delivery device embodies any of a number of techniques known to those skilled in the art for the controlled release of a treatment medium there from. In more specific embodiments, said another portion comprises a coating that is applied to an end segment of the delivery device first portion, which coating is configured or arranged so the treatment medium is controllably released there from. In further embodiments, the another portion of the delivery device embodies a sustained release device or structure whereby the treatment medium is eluted or diffused there from as well as structures whereby the treatment medium traverses the supporting/protecting structure via other known techniques such as osmosis.

In further embodiments, the delivery device first portion comprises a stent, plug type member or a coil member; one end of which is configured and arranged so as to be removably secured within the natural opening, more specifically the punctum. The other end of which is configured and arranged so as to form a structure to which is secured and/or applied the coating or member from which the treatment medium is controllable released. In specific embodiments, the stent, plug type member or coil member comprises a backbone, platform or support member to which the treatment medium coating is applied or to which the treatment medium member is secured.

In further embodiments, the treatment medium comprises mediums or agents in what ever form that are useable in connection with, but not limited to, the treatment of a wide range of disorders, diseases, and/or physiological problems of a mammalian eye. Such treatment mediums of the present invention in what ever form also are useable in connection with surgical procedures. Such treatment mediums include but are not limited to therapeutics and medicaments. Exemplary therapeutic mediums include, but are not limited to, thrombin inhibitors; antithrombogenic agents; thrombolytic agents; fibrinolytic agents; vasospasm inhibitors; calcium channel blockers; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 1,3-cis retinoic acid); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil); immunological drugs (such as vaccines and immune stimulants); hormonal agents (such as estrogens, estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotropin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; and other therapeutic agents such as prostaglandins, antiprostaglandin, prostaglandin precursors, and the like.

Antiproliferatives include any of a number of compounds, agents, therapeutic mediums or drugs known to those skilled in the art that inhibit the proliferation of cells. Such compounds, agents, therapeutic mediums or drugs include, but are not limited to, 5-fluorouracil, taxol, rapamycin, mitomycin C and cisplatin.

Neuroprotectives include any of a number of compounds, agents, therapeutic mediums or drugs known to those skilled in the art that guard or protect against neurotoxicity; the quality of exerting a destructive or poisonous effect upon nerve tissue. Such compounds, agents, therapeutic mediums or drugs include, but are not limited to, lubezole.

Anti-inflammatories include any of a number of compounds, agents, therapeutic mediums or drugs known to those skilled in the art, either steroidal or non-steroidal, and generally characterized has having the property of counteracting or suppressing the inflammatory process. Non-steroidal inflammatory drugs or compounds comprise a class of drugs that shares the property of being analgesic, antipyretic and anti-inflammatory by way of interfering with the synthesis of prostaglandins. Such non-steroidal anti-inflammatories include, but are not limited to, indomethacin, ibuprofen, naxopren, piroxicam and nabumetone. Such anti-inflammatory steroids contemplated for use in the methodology of the present invention, include triamcinolone acetonide (generic name) and corticosteroids that include, for example, triamcinolone, dexamethasone, fluocinolone, cortisone, prednisolone, flumetholone, and derivatives thereof (See also U.S. Pat. No. 5,770,589, the teachings of which are incorporated herein by reference).

As is known to those skilled in the art, growth factors is a collective term originally used to refer to substances that promote cell growth and is now loosely used to describe molecules that function as growth stimulators (mitogens) but also as growth inhibitors (sometimes referred to as negative growth factors), factors that stimulate cell migration, or as chemotactic agents or inhibit cell migration or invasion of tumor cells, factors that modulate differentiated functions of cells, factors involved in apoptosis, factors involved in angiogenesis, or factors that promote survival of cells without influencing growth and differentiation. In the present invention, such growth factors include, but are not limited to, pigment epithelium derived factor and basic fibroblast growth factor.

As is known to those skilled in the art, neurotropic factors is a general term used to describe growth factors and cytokines that can enhance neuronal survival and axonal growth and that regulate synaptic development and plasticity in the nervous system. In the present invention, such growth factors include, but are not limited to, ciliary neurotrophic factors and brain-derived neurotrophic factors.

Antiangiogenics include any of a number of compounds, agents, therapeutic mediums or drugs known to those skilled in the art that inhibit the growth and production of blood vessels, including capillaries. Such compounds, agents, therapeutic mediums or drugs include, but are not limited to, anecortave acetate and anti VEGF antibody.

Thrombolytics, as is known to those skilled in the art include any of a number of compounds, agents, therapeutic mediums or drugs that dissolve blot clots, or dissolve or split up a thrombus. Such thrombolytics include, but are not limited to, streptokinase, tissue plasminogen activator or TPA and urokinase.

Such treatment mediums also include fluticasone.

The treatment medium including therapeutics being delivered or administered is in any of a number of formulations including fluid solutions, solids and/or sustained release formulations or devices. In further embodiments, the sustained releases devices comprising said another portion of the delivery device of the present invention include, but are not limited to those having the following characteristics; flexible rods, thin films, foldable discs, biodegradable polymers with the therapeutic medium (e.g., drug) embedded within, drug eluting polymer coatings over a rigid scaffold, compressed drug "pellets" or a therapeutic medium encapsulated in a semi-permeable membrane. Also, some characteristic formulations for delivery of the treatment medium include, but are not limited to, injectable hydrogels, cyclodextrin "solubilized" and micronized solutions.

The another portion of the delivery device of the present invention can comprise a biocompatible capsules suitable for delivery of the therapeutic medium. Exemplary biocompatible polymer capsules contemplated for use in the methodology of the present invention comprise (a) a core or compartment which contains the therapeutic medium, either suspended in a liquid medium or immobilized within a biocompatible matrix, and (b) a surrounding jacket comprising a membrane that is biocompatible and permits diffusion of the drugs, therapeutics, medicaments such as proteins, cells or small molecule pharmaceuticals, or the like to the tissues of the eye. As indicated herein, the compartment can comprise a biocompatible matrix of a hydrogel or other biocompatible matrix material that stabilizes the position of the therapeutic medium. The jacket for the capsule may be manufactured from various polymers and polymer blends including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers, and mixtures thereof.

Methods according to the present invention include, but are not limited to pre-/post-operative treatment procedures in which a delivery device of the present invention is inserted into orifice or opening in the eye (e.g., punctum) prior to, during or subsequent to treatment medium prior to, during and/or subsequent to the operative/surgical procedure such that the treatment medium is dispensed prior to, during and/or subsequent to the surgical procedure. It also is contemplated that such methods includes inserting a plurality or more delivery devices at different times (e.g., before and during the surgical procedure) so the treatment medium can be appropriately set and/or adjusted to meet the particular needs of a given phase of the treatment process. Also, such methods contemplate inserting a plurality or more delivery devices at different times to adjust and control the constitution of the treatment medium to accommodate changing medical needs. For example, the treatment regime and thus the treatment medium may need to be changed to dispense an antibiotic or other therapeutic medium because of the presence of an infection or other medical condition (inflammation).

In addition, the methods of the present invention contemplate insertion of a delivery device in non-surgical cases, for treatment of a physiological condition, disease condition (e.g., infectious problem) or other condition of the eye (e.g., inflammatory disorders) treated by administering medicaments, therapeutics and the like. It also is contemplated that such methods includes inserting a plurality or more delivery devices at different times throughout the treatment regime or process so the treatment medium provided for administration can be appropriately set and/or adjusted to meet the particular needs of a given phase of the treatment process or regime. Thus, the medical personnel would remove the delivery device presently inserted in the opening and insert in its place another delivery device having a different constitution that the presently inserted device or to replace a spent or used up delivery device with a fresh delivery device.

In addition, to treatment of diseased eye conditions and or use in conjunction with surgical procedures, the methods of the present invention also contemplate insertion of a delivery device for prophylactic administration of a treatment medium over a short or long period of time. The methods of the present invention also contemplate administration of a treatment medium to the eye for prophylactic treatment of a physiological condition of an eye(s) such as for example, the treatment of the so-called dry-eye condition.

Also featured are systems embodying such delivery devices as well methods implementing the techniques and processes embodied in such delivery devices.

Other aspects and embodiments of the invention are discussed below.

BRIEF DESCRIPTION OF THE DRAWINGS

For a fuller understanding of the nature and desired objects of the present invention, reference is made to the following detailed description taken in conjunction with the accompanying drawing figures wherein like reference character denote corresponding parts throughout the several views and wherein:

FIG. 2C is a schematic view illustrating a treatment medium delivery device according to a third embodiment of the present invention;

FIG. 2D is a schematic view illustrating a treatment medium delivery device according to a fourth embodiment of the present invention;

FIG. 3A is a partial view of a first body portion of the present invention illustrating an example configuration of an end thereof;

FIG. 3B is a partial view of a first body portion of the present invention illustrating another example configuration of an end thereof;

FIG. 4 is a schematic view of a second body portion according to an embodiment of the present invention.

DETAILED DESCRIPTION OF THE INVENTION

Figure 1:
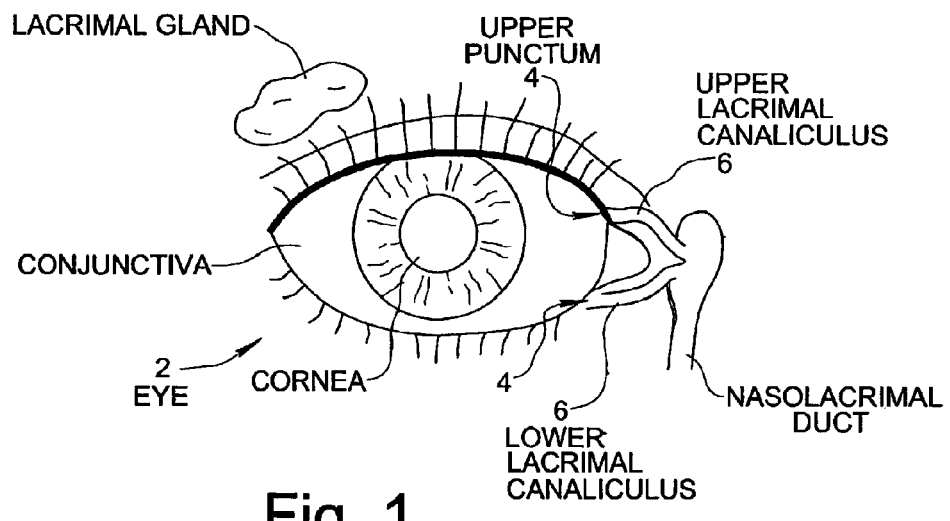
FIG. 1 is an illustrative view of an eye.
Figure 2A:
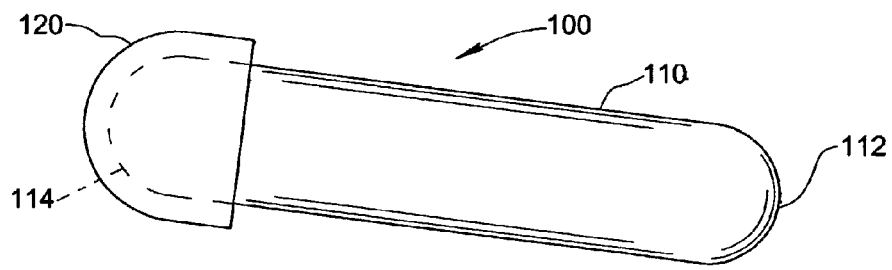
FIG. 2A is a schematic view illustrating a treatment medium delivery device according to a first embodiment of the present invention.

Referring now to the various drawing figures wherein like reference characters refer to like parts, there is shown in FIG. 2A a treatment medium delivery device 100 according to the present invention including a first body portion 110 and a second body portion 120. The second body portion 120 is generally configured and arranged so as to include the treatment medium that is to be dispensed to the exterior surface of an eye 2 (FIGS. 1, 5, and 6) being treated, the exterior surface includes but is not limited to the cornea and conjunctiva.

The first body portion 110 is sized, configured and arranged so as to be removably inserted, and secured in an opening provided in the eye, more particularly, a portion of the body proximal the eye. More particularly, the first body portion 110 is sized, configured and arranged such that when the first body portion is inserted into the opening it is secured within the opening so it does not fall or come out as a result of normal and expected bodily function, such as for example, blinking of the eyelids and any laxity of the eye. In particular exemplary embodiments, the opening in the eye is a punctum 4 (FIGS. 1, 5, and 6) of the eye 2 for a mammalian body that is fluidly, coupled to a lacrimal canaliculus 6 (FIGS. 1, 5, and 6) and the treatment medium delivery device of the present invention is configured and arranged so it remains secured within the punctum and a portion of the lacrimal canaliculus during normal eye function.

The first body portion 110 is configurable as a solid member, a member having a lumen or passage defined therein, a member having a passage passing through a portion of the first body portion, an open compartment located within the first body portion or a body structure that corresponds in great part to the structure of a conventional stent (see FIG. 2D). As is known to those skilled in the art, a stent provides a scaffold like structure that can be arranged to form a generally cylindrical shape or a shape that conforms to the opening and passage the stent is being inserted into. The term "stent," as used herein, includes any scaffold like structures as well as conventional stents. The first body portion 110 also is constructed of any of a number of biocompatible materials as is known to those skilled in the art, including metals such as stainless steel and nitinol (nickel-titanium) and plastics that have strength and material characteristics suitable for the intended use. Such materials of the first body portion 110 also preferably are characterized as being non-toxic and non-sensitizing.

Such a first body portion 110 also is sized and arranged so that medical personnel can grasp the delivery device 100 using any of a number of medical instruments (e.g., forceps, clamp) and to manipulate the first body portion 110 so it is inserted into the opening without causing the first body portion to break or to deform during such insertion to the extent that it would prevent removal of the first body portion from the opening. Such a first body portion 110 also is sized and arranged so the medical personnel can grasp the delivery device 100 at a later time thereby allowing the delivery device, more particularly the inserted part of the first body portion to be removed or extracted from the opening without structural failure. Preferably such insertion and extraction also is accomplished without causing significant injury to the tissues of the opening about and proximal to the entry site thereof.

In more particular embodiments, the first body portion includes an end 112 that is configured to facilitate insertion of the first body portion 110 into the opening as well as to minimize significant trauma and/or injury to the tissue of the opening as the first body portion is being inserted therein. In specific exemplary embodiments, the first body portion end 112 is arcuate and/or generally hemispherical. It is contemplated and within the scope of the present invention for the first body portion end 112 to be configured so it presents an end that is appropriate for the intended function and use. For example, the end 112 is configurable so as to have a piercing capability if the function and use of the first end portion 110 would involve piercing of tissue or a membrane as the first portion end is being inserted into the body opening.

In further embodiments, a second end 114 of the first body portion 110 is arranged so as to form a platform, structure, scaffold or support for the second body portion 120. As such the first body portion second end 114 is configurable so as to form any of a number of arrangements or configurations suitable for the use/application. With reference also to FIGS. 3A, B; such arrangements for the first body portion second ends 114, 114a, 114b, include, but are not limited to; an extension of the first body portion 110 (as illustrated in FIG. 2A), a rod 115 extending from a surface of the first body portion 110a (as illustrated in FIG. 3A), a plurality of rods 115a-c extending from a surface of the first body portion 110b (as illustrated in FIG. 3B) or one or more outwardly extending elements of any geometric cross-section; where each of the rods and/or outwardly extending elements having a cross-section smaller than the cross-section or diameter of the first body portion.

In an embodiment of the present invention, the second body portion 120 comprises a member, device (e.g., an eluting device, a sustained released device, an encapsulation device) or coating that is applied, secured, attached or bonded to the first body portion second end 114 using any of a number of techniques known to those skilled in the art such as adhesives. Such a second body portion 120 is constituted so as to carry one or more treatment mediums, for example analgesics, an antibiotic or a medicament or medium used for treating dry eye condition, and provide a delivery vehicle or structure, such as a matrix or medium, that is constituted so it releasably retains the one or more treatment mediums therein so the medium can be released there from under predetermined conditions. Such releasably retaining includes but is to limited to encapsulation of the treatment medium(s) within the structure comprising the delivery vehicle or structure. It also is contemplated that the second body portion 120 can comprise a medium or material, for example a polymer, that is formed, cured or otherwise appropriately processed such that it is bonded to the first body portion second end 114*a-c*, as a result of such forming, curing, polymerizing or processing.

Preferably, the delivery vehicle or structure is further constituted so the treatment medium being releasably retained therein is released from the vehicle or structure at a controlled or essentially controlled process, more preferably releasing the treatment medium without significantly affecting the properties or activity of the treatment medium's active element(s) or constituents. In illustrative exemplary embodiment, the one or more treatment mediums are released to the fluid found on the eye, more specifically the tears secreted by the bodily structures and glands making up a mammalian eye. In particular embodiment, the delivery vehicle or structure also is constituted so it is characterized as being generally biocompatible, non-toxic and non-sensitizing.

In an illustrative exemplary embodiment, the second body portion 120 can be constituted of a biodegradable polymers containing microparticles of the treatment medium such as that described for example, in U.S. Pat. No. 5,098,443 the teachings of which are incorporated herein by reference. In another exemplary embodiment, and with reference to FIGS. 2C, 4, the second body portion 120*c* is formed so as to include one or more compartments or chambers 122 therein, where each of the one or more compartments includes one or more treatment mediums (e.g., different treatment mediums 126*x*, 126*y*, 126*z* disposed in different chambers 122).

The surrounding part 124 of the second body portion 120*c* can comprise a polymeric material whereby the treatment medium is slowly released thereof by osmosis as suggested in U.S. Pat. No. 5,098,443. In an alternative embodiment, the second end portion 120 can be configured and arranged so as to function much like membrane diffusion drug delivery system such as that described in U.S. Pat. No. 5,378,475 or U.S. Pat. No. 5,466,233 the teachings of which are incorporated herein by reference. For example, the surrounding part 124 would comprise two coatings with different permeabilities, whereby the treatment medium diffuses through a small opening in one of these coatings achieving near-order release kinetics.

In yet another embodiment, the second body portion including the chamber 122 and the surrounding portion 124 thereof are configurable so as to essentially form any of a number of biocompatible capsules as is known in the art that are suitable for delivery of the therapeutic medium. In exemplary embodiments, the chamber 122 corresponds to the compartment of the biocompatible polymer capsules that contains the treatment medium, either suspended in a liquid medium or immobilized within a biocompatible matrix, and (b) the surrounding part 124 corresponds to the surrounding jacket that comprises a membrane that is biocompatible and permits diffusion of the treatment medium (e.g., drugs, therapeutics, medicaments such as proteins, cells or small molecule pharmaceuticals, or the like) to the tissues of the eye. As indicated herein, the chamber 122 also can be constituted so it includes a biocompatible matrix of a hydrogel or other biocompatible matrix material that stabilizes the position of the therapeutic medium. The surrounding part 124 or surrounding jacket may be manufactured from various polymers and polymer blends including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers, and mixtures thereof.

Figure 2B:
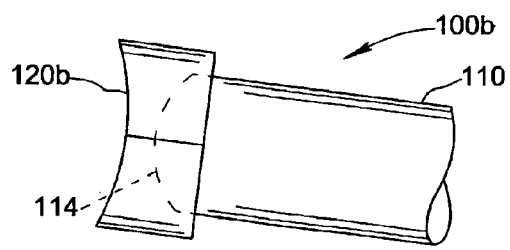
FIG. 2B is a schematic view illustrating a treatment medium delivery device according to a second embodiment of the present invention.

Now referring also to FIG. 2B, the second body portion 120*b* is configurable so as to present any of a number of surface arrangements or profiles that are otherwise appropriate for the intended use. As shown in FIG. 2A, the second body portion 120 is configurable so as to present a cylindrical profile with an arcuate or generally hemispherical end. Alternatively, and as shown in FIG. 2B, the end profile of the second body portion 120*b* while arcuate is arranged so as to be concave or dished like, whereby for example, the fluid in the eye can repose and remain in contact with the second body portion 120*b*. In more particular embodiments, the second body portion 120 also is configured and shaped so as to present a non-traumatic end profile so as to minimize trauma and or injury to tissues or body features (e.g., eyelids), that can come in contact with the second body portion 120 when the delivery device is removably secured within the bodily opening (e.g., punctum).

In further embodiments, the second body portion 120 is configurable so a portion thereof comprises a non-linear shaped member have multiple turns or angles, for example at least two, three, four, five, six, seven, right, nine or ten separate deviations from a linear path. Such a non-linear shaped member comprises a coil shape, random curled shapes, a zigzag shape, a "J" shape, a "C" shape and the like.

Although the first body portion 110 is generally illustrated in FIGS. 2A,B as a extending along a long or longitudinal axis, this shall not be construed as limiting a delivery device of the present invention to the illustrated structure. It is contemplated and within the scope of the present invention for the first body portion to be configured and arranged within any of a number of configurations and shapes known to those skilled in the art that are consistent with the intended use and function of the present invention.

In the embodiment shown in FIG. 2C, the first body portion 110*c* is configured so as to comprise a continuous coil structure made up of a plurality of coil turns 113 that curl about the longitudinal axis of the first body portion. Such a coiled first body portion 110*c* also is configured and arranged so that the characteristics and properties (e.g., spring constant) of the coiled structure is such that the coiled first body portion has sufficient axial and/or radial rigidity so that it can be inserted into the opening without significant bending or deformation of the coiled structure during such insertion, thereby minimizing trauma or significant injury to the tissues at the entry site. In addition, the coiled structure also has sufficient axial and/or radial rigidity to also allow the coiled first body portion 110c to be retracted or removed from the opening while also minimizing trauma or significant injury to the tissues during such retraction. As also illustrated in FIG. 2C, the second body portion 120c is attached, secured, bonded or applied to an end 114 of the coiled first body portion 110c using any of a number of techniques known to those skilled in the art.

FIG. 2D shows a delivery device 100d formed in accordance with another embodiment of the present invention. Delivery device 100d comprises a first body portion 110d in the form of a stent 117 having a passageway or lumen 119, and a second body portion 120d in the form of a compressed drug pellet. As described earlier, the different forms of the first body portion and second body portion may be used with each other in any suitable combination for the particular application; for example, a first body portion comprising a stent may be combined with a second body portion in the form of a coating (i.e. the coating may be applied to an end of the stent).

In further refinement of the present invention, the first and second body portions 110, 120 are configured and arranged so either of the two portion or the combination of the two portions create a delivery device 100 that occludes, blocks or plugs the body opening (e.g., punctum) in which at least a part of the first body portion 110 is inserted into, thereby also occluding, blocking or plugging any passage, duct or other bodily feature to which the opening is fluidly coupled to. In this way, the treatment medium is retained in proximity to the external surface(s) of the eye and is essentially prevented from leaving the treatment site via the blocked passage or duct. Alternatively, the first and second body portions 110, 120 are configured and arranged such that the second body portions rests on the punctum and the device 100 does not occlude the punctum.

Thus, the treatment medium being delivered by the delivery device 100 of the present invention is not diluted or reduced because of drainage from the eye through the nasolacrimal duct as is experienced or seen with the use of conventional techniques for the topical administration of treatment mediums including therapeutics and medicaments. Thus, in comparison to conventional techniques the amount of the treatment medium that is available for treatment is not also thereby reduced. Consequently, the dosage or amount of treatment medium to be released from a delivery device 100 of the present can be reduced as compared to conventional devices or conventional techniques thereby also reducing the potential or risk of unwanted systemic side effects. Further, the increased retention time of the treatment medium when using the delivery device of the present invention as compared to that seen using conventional topical administration techniques and/or devices allows a more effective treatment protocol to be established.

In addition, the delivery device of the present invention overcomes a number of the shortcomings of conventional topical insets. As indicated herein, such topical inserts are such that they are easily removed from the eye and also require action on the part of the patient to periodically replace the insert as it is used up as well as when the insert falls out. In contrast, the delivery device 100 of the present invention is configured and arranged so it remains secured within the body opening (e.g., punctum) during normal bodily processes and functions.

Also, because the treatment medium available for treatment using the delivery device of the present invention is increased as compared to that available when using prior art devices or inserts, the periodicity of replacement is decreased (i.e., time between removal and replacement increased). Thus, it becomes possible when using a delivery device of the present invention for the process of removing an old delivery device and inserting a new delivery device to be performed by trained medical personnel instead of the patient.

In the foregoing discussion the delivery device 100 of the present invention is described as occluding the passage or duct associated with the opening in which the deliver device is inserted. It also is contemplated and thus within the scope of the present invention, however, for the first and second body portions 110, 120 to be further configured and arranged so that a lumen or passage is created within the deliver device that in effect re-opens the occluded passage or duct, at least to some degree, after the treatment medium is spent. In this way, for example, the punctum is effectively re-opened thereby allowing drainage of fluid to the tear ducts 6 (FIG. 6) thus allowing the patient to regain drainage function to some extent without requiring the patient to return to the medical personnel for removal of the delivery device immediately or shortly after completion of the treatment process.

In further embodiments, the treatment medium comprises mediums or agents in what ever form that are useable in connection with, but not limited to, the treatment of a wide range of disorders, diseases, and/or physiological problems of a mammalian eye. Such treatment mediums of the present invention in what ever form useable in connection with surgical procedures. Such treatment mediums include but are not limited to therapeutics and medicaments. Exemplary therapeutic mediums include, but are not limited to, thrombin inhibitors; antithrombogenic agents; thrombolytic agents; fibrinolytic agents; vasospasm inhibitors; calcium channel blockers; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; anti-proliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluorometholone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 1,3-cis retinoic acid); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine demecarium bromide); antineoplastics (such as carmustine, cisplatin, fluorouracil); immunological drugs (such as vaccines and immune stimulants); hormonal agents (such as estrogens, estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotropin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, and the like.

Antiproliferatives include any of a number of compounds, agents, therapeutic mediums or drugs known to those skilled in the art that inhibit the proliferation of cells Such compounds, agents, therapeutic mediums or drugs include, but are not limited to, 5-fluorouracil, taxol, rapamycin, mitomycin C and cisplatin.

Neuroprotectives include any of a number of compounds, agents, therapeutic mediums or drugs known to those skilled in the art that guard or protect against neurotoxicity; the quality of exerting a destructive or poisonous effect upon nerve tissue. Such compounds, agents, therapeutic mediums or drugs include, but are not limited to, lubezole.

Anti-inflammatories include any of a number of compounds, agents, therapeutic mediums or drugs known to those skilled in the art, either steroidal or non-steroidal, and generally characterized has having the property of counteracting or suppressing the inflammatory process. Non-steroidal inflammatory drugs or compounds comprise a class of drugs that shares the property of being analgesic, antipyretic and antiinflammatory by way of interfering with the synthesis of prostaglandins. Such non-steroidal anti-inflammatories include, but are not limited to, indomethacin, ibuprofen, naxopren, piroxicam and nabumetone. Such anti-inflammatory steroids contemplated for use in the methodology of the present invention, include triamcinolone acetonide (generic name) and corticosteroids that include, for example, triamcinolone, dexamethasone, fluocinolone, cortisone, prednisolone, flumetholone, and derivatives thereof (See also U.S. Pat. No. 5,770,589, the teachings of which are incorporated herein by reference).

As is known to those skilled in the art, growth factors is a collective term originally used to refer to substances that promote cell growth and is now loosely used to describe molecules that function as growth stimulators (mitogens) but also as growth inhibitors (sometimes referred to as negative growth factors), factors that stimulate cell migration, or as chemotactic agents or inhibit cell migration or invasion of tumor cells, factors that modulate differentiated functions of cells, factors involved in apoptosis, factors involved in angiogenesis, or factors that promote survival of cells without influencing growth and differentiation. In the present invention, such growth factors include, but are not limited to, pigment epithelium derived factor and basic fibroblast growth factor.

As is known to those skilled in the art, neurotropic factors is a general term used to describe growth factors and cytokines that can enhance neuronal survival and axonal growth and that regulate synaptic development and plasticity in the nervous system. In the present invention, such growth factors include, but are not limited to, ciliary neurotrophic factors and brain-derived neurotrophic factors.

Antiangiogenics include any of a number of compounds, agents, therapeutic mediums or drugs known to those skilled in the art that inhibit the growth and production of blood vessels, including capillaries. Such compounds, agents, therapeutic mediums or drugs include, but are not limited to, anecortave acetate and anti VEGF agents or the activity sites of anti VEGF agents. Anti VEGF agents include, but are not limited to, Macugen, Lucentis, Avastin, Squalamine, and Kenalog.

Thrombolytics, as is known to those skilled in the art include any of a number of compounds, agents, therapeutic mediums or drugs that dissolve blot clots, or dissolve or split up a thrombus. Such thrombolytics include, but are not limited to, streptokinase, tissue plasminogen activator or TPA and urokinase.

Such treatment mediums also include fluticasone.

The treatment medium including therapeutics being delivered or administered is in any of a number of formulations including, fluid solutions, solids and/or sustained release formulations or devices. In further embodiments, the sustained releases devices comprising said another portion of the delivery device of the present invention include, but are not limited to those having the following characteristics; flexible rods, thin films, foldable discs, biodegradable polymers with the therapeutic medium (e.g., drug) embedded within, bioerodable materials, drug eluting polymer coatings over a rigid scaffold, compressed drug "pellets" or a therapeutic medium encapsulated in a semi-permeable membrane. Also, some characteristic formulations for delivery of the treatment medium include, but are not limited to, injectable hydrogels, cyclodextrin "solubilized" and micronized solutions.

Figure 5:
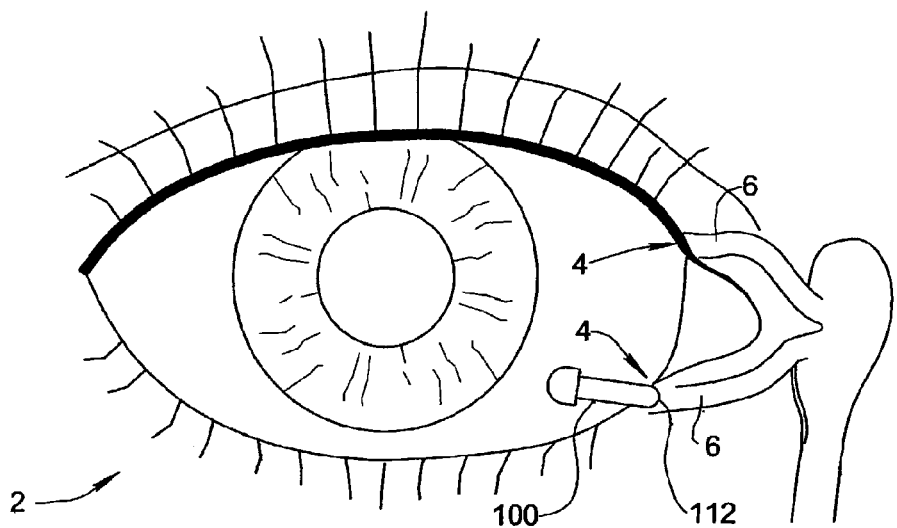
FIGS. 5 and 6 are various view of an eye showing insertion of a treatment delivery device according to the present invention in the punctum.
Figure 6:
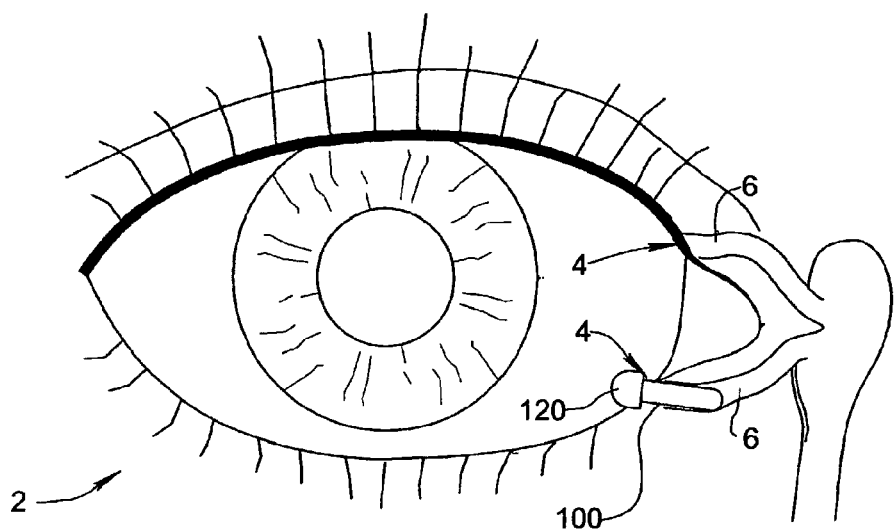

The use of any of the herein described delivery devices 100, 100*b*, 100*c*, 100*d* of the present invention as well as the methods for treating a wide range of disorders and diseases of the eye as well as pre-operative and post-operative administration of a wide range of therapeutics and treatments mediums and/or agents can be understood from the following discussion with reference to FIGS. 5, 6. The methodologies of the present invention shall be understood to include, but not limited to, (a) pre- and post-operative treatments associated with Lasik, cataract or refractive procedures or glaucoma procedures as is known to those skilled in the art including but not limited to the administration of anti-inflammatory therapeutics (e.g., steroidal anti-inflammatory drugs) and anti-infective therapeutics, including antibiotics; (b) post operative treatments and delivery of topical drugs associated with the post operative management of corneal transplants; (c) treatment of corneal disorders such as corneal melts by topical administration of drugs; (d) treatment of inflammatory disorders or infectious problems of the eye (e.g., conjunctivitis) by topical administration of anti-inflammatory therapeutics or anti-infective therapeutics; and/or (e) treatment of dry eye over a short or long period of time with artificial tears, Restasis, allergen or other agents known to those skilled in the art as well post-operative treatments in which desired levels of moisture are to be maintained (e.g., post-operative associated with cataract procedures).

Reference also should be made to the foregoing discussion for FIGS. 2-4 for features of a delivery device of the present invention not otherwise shown in FIGS. 5 and 6. In addition, while reference is made in the following discussion to the delivery device 100 shown in FIG. 2A, this shall not be construed as limiting the methodologies of the present invention to this delivery device as such methodologies are usably with any of the delivery devices described herein as well as any embodiments and aspect thereof also described herein or reasonably inferable from the teachings provided herein.

Prior to insertion, the medical personnel would remove the treatment delivery device 100 from any protective packaging and ready the delivery device for insertion into the bodily opening, in the illustrated embodiment the punctum 4. In addition, the medical personnel (e.g., surgeon) would take those other actions required to make the punctum 4 ready for such insertion.

Thereafter the medical personnel would grasp the delivery device 100 using any of a number of devices known to those skilled in the art such as for example forceps or clamps. The medical personnel would then manipulate the delivery device so the first end 112 of the first body portion 110 is proximal the punctum 4 and then insert such first end into the opening of the punctum. The medical personnel would continue to insert the first body portion 110 into the punctum so the delivery device is secured within the punctum and retained by the associated lacrimal canaliculus as well as so the second body portion 120 is appropriately positioned to minimize trauma and/or injury to the tissues of the eye after such insertion is completed.

After the expiration of a predetermined period of time, the medical personnel would assess the progress of treatment as well as the assessing any post-operative conditions of the eye. If further treatment is needed, or the type and/or quantity of treatment medium being dispensed needs to be adjusted, the medical personnel would extract the presently inserted treatment medium delivery device 100 from the punctum and insert another treatment delivery device therein, which device is constituted so as to be capable of dispensing the desired type and/or amount of treatment medium. If the treatment process is complete, then the medical personnel would remove the presently inserted delivery device 100 from the punctum.

Although a preferred embodiment of the invention has been described using specific terms, such description is for illustrative purposes only, and it is to be understood that changes and variations may be made without departing from the spirit or scope of the following claims.

All patents, published patent applications and other references disclosed herein are hereby expressly incorporated by reference in their entireties by reference.

Those skilled in the art will recognize, or be able to ascertain using no more than routine experimentation, many equivalents of the specific embodiments of the invention described herein. Such equivalents are intended to be encompassed by the following claims.

What is claimed is:

1. A device for delivering a treatment medium to an eye, comprising:
    a first body portion and a second body portion;
    wherein the first body portion is configured and arranged to be removably secured within a natural opening comprising a single punctum of the eye; and
    wherein the second body portion comprises a coating that is applied to an end segment of the first portion, which coating is configured or arranged so the treatment medium is controllably released therefrom to the eye;
    and wherein the delivery device is configured and arranged such that when at least a part of the first body portion is removably inserted into the punctum, the device occludes or plugs the punctum.

2. The device of claim 1, wherein the treatment medium comprises a prostaglandin.

3. The device of claim 2, wherein the first body portion includes a plug type member, one end of which is configured and arranged so as to be removably secured within the punctum.

4. The device of claim 3, wherein the first body portion includes an end which is configured and arranged so as to form a structure to which is applied the coating from which the treatment medium is controllably released.

5. The device of claim 4, wherein the first body portion comprises a lumen or an open compartment located within the first body portion.

6. The device of claim 5, wherein the treatment medium is delivered in a controllable manner over a predetermined time period directly to the eye.

7. The device of claim 1, wherein the treatment medium is retained in proximity to the external surface of the eye and is prevented from leaving the treatment site via the blocked punctum.

8. The device of claim 1, wherein the treatment medium is selected from the group consisting of thrombin inhibitors; antithrombogenic agents; thrombolytic agents; fibrinolytic agents; vasospasm inhibitors; calcium channel blockers; vasodilators; antihypertensive agents; antimicrobial agents; inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives; anticancer chemotherapeutic agents; anti-inflammatories; non-steroidal anti-inflammatories; antiallergenics; antiproliferative agents; decongestants; miotics and anticholinesterase; antineoplastics; immunological drugs; hormonal agents; immunosuppressive agents; growth hormone antagonists; growth factors; inhibitors of angiogenesis; dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; prostaglandins; anti-prostaglandins; prostaglandin precursors and combinations thereof.

9. The device of claim 1, wherein the first body portion comprises a first end that is configured to facilitate insertion of the first body portion into the punctum.

10. The device of claim 1, wherein the first body portion comprises a second end that is configured to form a support for the second body portion.

11. The device of claim 1, wherein the first body portion extends along a longitudinal axis.

12. A method for treating an eye, comprising:
    providing a delivery device according to claim 1; and
    inserting the first portion of the delivery device into a punctum of the eye such that the first portion is retained by a single lacrimal canaliculus of the eye and the second portion of the delivery device is adjacent to an external surface of the eye.

* * * * *